United States Patent [19]

Hansen

[11] E Re. 31,268

[45] Reissued Jun. 7, 1983

[54] METHOD OF RECOVERING IMMUNOGLOBULIN USING A POLYOL AND AN ALKANOIC ACID

[75] Inventor: Jorgen F. Hansen, Rodovre, Denmark

[73] Assignee: Nordisk Insulinlaboratorium, Gentofte, Denmark

[21] Appl. No.: 292,386

[22] Filed: Aug. 13, 1981

Related U.S. Patent Documents

Reissue of:

[64] Patent No.: 4,164,495
Issued: Aug. 14, 1979
Appl. No.: 914,456
Filed: Jun. 12, 1978

U.S. Applications:

[63] Continuation of Ser. No. 782,255, Mar. 28, 1977, abandoned.

[30] Foreign Application Priority Data

Apr. 6, 1976 [DK] Denmark ..... 1628/76

[51] Int. Cl.[3] ..... A61K 37/04; A61K 37/06; C07G 7/00

[52] U.S. Cl. ..... 260/112 B; 424/101; 424/177

[58] Field of Search ..... 260/112 B; 424/101, 424/177

[56] References Cited

U.S. PATENT DOCUMENTS

| | | | |
|---|---|---|---|
| 3,100,737 | 8/1963 | Auerswald | 260/112 B X |
| 3,415,804 | 12/1968 | Polson | 260/112 B |
| 3,686,395 | 8/1972 | Stephan | 424/101 |
| 3,770,631 | 11/1973 | Fekete et al. | 424/101 X |
| 3,808,189 | 4/1974 | Breuer | 260/112 B |
| 3,869,436 | 3/1975 | Falksveden | 260/122 B |
| 3,876,775 | 4/1975 | Izaka et al. | 424/177 |
| 3,880,989 | 4/1975 | Garcia | 260/112 B X |
| 3,916,026 | 10/1975 | Stephan | 424/177 |
| 4,017,470 | 4/1977 | Izaka et al. | 260/112 B |
| 4,021,540 | 5/1977 | Pollack et al. | 260/112 B X |
| 4,075,193 | 2/1978 | Campbell et al. | 260/112 B |
| 4,082,734 | 4/1978 | Stephan | 260/112 B |
| 4,093,606 | 6/1978 | Coval | 260/112 B |
| 4,124,576 | 11/1978 | Coval | 260/112 B |
| 4,154,819 | 5/1979 | Stephan | 260/112 B X |

OTHER PUBLICATIONS

J. of Immunology, 1962, Frommhagen et al., pp. 336–343 (1962).

Vox Sang., 34:143–148 (1978), Gislason et al.

Encycl. of Chemistry, 3rd Ed. (1973), pp. 466–477, Hampel et al.

Rev. Franc. Etudes Clin. et Biol. 1969, XIV, pp. 1054–1058, Steinbuch et al.

*Primary Examiner*—Howard E. Schain
*Attorney, Agent, or Firm*—Ladas & Parry

[57] ABSTRACT

Immunoglobulins or gammaglobulins are recovered in a pure and anticomplementary condition by fractionated precipitation of blood plasma with a polycondensed di or polyol, such as PEG, in the presence of a mono or polyalkanoic acid having 4 to 12 carbon atoms, such as caprylic acid.

5 Claims, No Drawings

METHOD OF RECOVERING IMMUNOGLOBULIN USING A POLYOL AND AN ALKANOIC ACID

Matter enclosed in heavy brackets [ ] appears in the original patent but forms no part of this reissue specification; matter printed in italics indicates the additions made by reissue.

This is a continuation of application Ser. No. 782,255 filed Mar. 28, 1977 and now abandoned.

The present invention relates to a method of recovering immunoglobulin suitable for intravenous administration, by fractionated precipitation of blood plasma, serum or a fraction thereof with a polycondensed di or polyol.

Immunoglobulins comprising gammaglobulins have therapeutic merit as they are suitable for preparing immunizing preparations.

Immunoglobulin is found in blood plasma of animal origin, from which it may be recovered by various precipitation and purification processes. Hence, gammaglobulin can be recovered as concentrated solutions by a method developed by Cohn et al, cf. J. Clin. Invest. Chem. Soc., 68, 479–75 (1946). According to Cohn, it is possible to obtain a fraction II being a 16.5% concentrate and which may be injected intramuscularly.

In the said prior-art method there are formed molecule aggregates of gammaglobulin rendering the products unsuitable for intravenous administration. Hence, Cohn's method comprises precipitation with alcohol which has a water-expelling effect and may lead to irreversible denaturation, whereby the globulin is rendered anti-complementary. It has been attempted to avoid this by means of special separation processes and/or by chemical modification of the gammaglobulin.

Hence, the prior art teaches an improved fractionating process in which the gammaglobulin is precipitated from blood plasma by means of polyethylene glycol (PEG) as precipitant, cf. U.S. Pat. No. 3,415,804. This eliminates the undesired denaturation, but the purity of the precipated product is unsatisfactory.

According to Danish Patent Application No. 6355/73, this precipitation process may be improved by replacing polyethylene glycol by a block copolymer of ethylene oxide and polyoxypropylene polymer of a further specified nature and observing some specific precipitation conditions.

In this manner it is possible to improve the yield by recovery of gammaglobulin. The precipitated products, however, are not always of satisfactory purity with sufficiently low anticomplementary activity.

The present invention is based on the observation that the fractionated precipitation of immunoglobulins, also known as gammaglobulins, by means of polyethylene glycol or other polycondensed di or polyol may be rendered appreciably more specific if the precipitation is carried out in the presence of a mono or polyalkanoic acid having from [4 to 12] *6 to 9* carbon atoms, whereby i.a. fibrinogen and lipoproteins are removed.

In the method according to the invention there is obtained in a simple manner purified immunoglobulin of a surprisingly high degree of purity coupled with a high yield. The yield equals that which it is possible to obtain by the best of the aforesaid methods.

The claimed method may be used in connection with any polycondensed di or polyglycol such as polyethylene glycol of varying molecular weights, e.g. 2000 to 12000, preferably 4000 to 6000, or polypropylene glycol. Also copolymers of ethylene oxide with propylene oxide or polyethers are suitable. [Suitable as mono or polyalkanoic acid is any alkanoic acid having from 4 to 12 carbon atoms.] Preferred according to the invention is an alkanoic acid having from 6 to 9 carbon atoms, preferably caprylic acid. Examples of other suitable alkanoic acids are caproic acid and nonanic acid. Also branched alkanoic acids may be used. When using higher alkanoic acids, [such as having from 9 to 12 carbon atoms,] it may be advantageous to incorporate additionally one or more carboxyl groups with a view to improving water-solubility. The same effect is achieved by using alkanoic acids having substituents containing, for example, one or more hydroxyl groups or amino groups.

The immunoglobulin-containing solution is advantageously mixed with from 1 to 8 percent by weight of polyethylene glycol or other polycondensed diol or polyol together with from 0.1 to 5 percent by weight of caprylic acid or other alkanoic acid having from [4 to 12] *6 to 9* carbon atoms, the precipitation with alkanoic acid according to the invention being advantageously effected at a pH of from 3 to 7, preferably from 4.5 to 5.5.

The method according to the invention will now be further illustrated below by means of some examples.

EXAMPLE 1

415 ml of human blood plasma containing 10 g of immunoglobulin per liter plasma are adjusted to a pH of 5.0 PEG 3000 is added until a concentration of 6 percent, and the solution is left to stand for 45 minutes. The precipitate, being mainly fibrinogen, is separated by centrifugation, and the liquid phase is adjusted to a pH of 7.0. After adding additional PEG 3000 to obtain a concentration of 12 percent, the mixture is left to stand for 45 minutes. The mixture is now centrifugated and the liquid phase containing albumin and alpha and beta-globulin is removed. The precipitate consisting of impure immunoglobulin is redissolved in an 0.9 percent sodium chloride solution to obtain a protein concentration of about 4 percent. The solution is filtered until clear using a Seitz EK-filter. The solution formed is admixed with 5 g of caprylic acid and 30 g of PEG 3000 per liter solution, and adjusted to a pH of 4.9. After leaving to stand for 2 hours at 20° C. the mixture is centrifugated, and the liquid phase is filtered to obtain a clear solution. This solution is adjusted to pH=7.0, and PEG 3000 is added until a concentration of 12 percent PEG. This results in precipitation of pure immunoglobulin which is recovered by centrifugation and drying. The yield of product is 60 percent. The degree of purity as determined by DISC PAGE (with 5 percent polyacrylamide) discloses substantially only two bands corresponding to IgG and IgM, respectively. The analysis is performed by application of 500 μg of product.

In Grabar and William's immunoelectrophoresis, using rabbit antibody against total human serum protein, there is found substantially only three arches, corresponding to IgG, IgM and IgA, respectively.

The purified product may, if desired, be converted to an intravenously injectable preparation by dissolution in 0.9 percent sodium chloride solution until a protein concentration of about 5 percent. The preparation is distinguished by an extremely low anticomplementary activity, for which reason it is particularly suitable for intravenous administration.

EXAMPLE 2

The procedure according to Example 1 is repeated, except that the human blood plasma is replaced by swine plasma.

EXAMPLE 3

The procedure according to Example 1 is repeated, except that human blood plasma is replaced by blood serum.

EXAMPLE 4

100 l of plasma or serum are mixed with 100 l of 600 g/l PEG 3000 solution. The pH is adjusted to 6.5. The precipitate is separated by centrifugation and redissolved in 100 l of distilled water admixed with 0.015 M of NaCl. There is added 40 g of PEG 3000 per liter and 5 g of caprylic acid per liter. The pH is adjusted to 5.0. Standing time 45 minutes. The precipitate is separated by centrifugation. The centrifugate is admixed with additional 40 g of PEG 3000 per liter. The pH is adjusted to 7.5. The precipitate is separated by centrifugation and redissolved in distilled water with 0.002 M of NaCl. The solution is filtered to clarity (e.g. SEITZ ® EK-Filter). The protein concentration should be 50–100 g/l. 20 g of DEAE-Sephadex-A25 ® are added per 100 g of protein. After leaving to stand for 60 minutes while stirring the DEAE-Sephadex is separated by filtration. The DEAE-Sephadex treatment is repeated. After sterile filtration there is obtained an immunoglobulin G preparation free from anticomplementariness and suitable for intravenous administration.

What I claim is:

1. A method of recovering purified immunoglobulin suitable for intravenous administration wherein blood plasma, serum or a fraction thereof is subjected to a fractionated precipitation using a combination of polycondensed polyol and a mono or polyalkanoic acid having from [4 to 12] *6 to 9* carbon atoms as a precipitant, the fractionating process being performed at approximately room temperature.

[2. A method according to claim 1, characterized in that the mono or polyalkanoic acid is an alkanoic acid having from 6 to 9 carbon atoms.]

3. A method according to claim 1 [or claim 2,] characterized by effecting the precipitation with alkanoic acid at a pH of from 3 to 7.

4. A process according to claim 1 wherein the polyol is a diol.

5. A method according to claim 3 wherein the pH is from 4.5 to 5.5.

6. A method according to claim [2] *1* wherein the alkanoic acid is caprylic acid.

* * * * *